United States Patent
Brown

(10) Patent No.: US 6,202,645 B1
(45) Date of Patent: Mar. 20, 2001

(54) CONTROL VALVE ACTUATED BY LOW-PRESSURE AND LOW-FLOW RATE CONTROL FLUID

(75) Inventor: Robert N. Brown, Los Gatos, CA (US)

(73) Assignee: Porter Instruments, Inc., Hatfield, PA (US)

( * ) Notice: Subject to any disclaimer, the term of this patent is extended or adjusted under 35 U.S.C. 154(b) by 0 days.

(21) Appl. No.: 09/257,470

(22) Filed: Feb. 25, 1999

(51) Int. Cl.[7] .......................................... A62B 9/02
(52) U.S. Cl. ................................ 128/205.24; 128/205.18
(58) Field of Search ..................................... 137/907, 908; 128/205.24, 205.18, 204.18, 203.14, 205.16, 207.12, 207.16, 204.26, 910, 203.12, 203.25; 251/63, 31

(56) References Cited

U.S. PATENT DOCUMENTS

| | | | |
|---|---|---|---|
| 5,103,854 | * 4/1992 | Bailey et al. | 137/102 |
| 5,632,298 | * 5/1997 | Artinian | 137/102 |

* cited by examiner

Primary Examiner—Aaron J. Lewis
Assistant Examiner—Teena Mitchell

(74) Attorney, Agent, or Firm—John F. A. Earley; John F. A. Earley, III; Harding, Earley, Follmer & Frailey

(57) ABSTRACT

A control valve actuated by a low-pressure/low-flow-rate control fluid. The valve housing has a control-fluid channel, a second-fluid channel, and a piston which is movable between open positions and a closed limit position. The valve has a piston head seat located intermediate the control-fluid channel. The seat has a shape which compliments the piston head so that the control fluid can flow through the control-fluid channel when the piston is in an open position. The valve has a piston stem seat located intermediate the second-fluid channel. The piston stem seat has a shape which compliments the free end of the piston stem so that a fluid seal is formed in the second-fluid channel when the piston is in the closed limit position and so that a second fluid may flow through the second-fluid channel when the piston is in an open position. The valve is constructed and arranged so that a low-pressure/low-flow-rate control fluid connected to the input port of the control-fluid channel will actuate the piston from the closed limit position to an open position. The valve is also constructed and arranged so that the second-fluid channel is automatically opened when the piston is moved to an open position, and the second-fluid channel is automatically closed when the piston is moved to the closed limit position.

1 Claim, 5 Drawing Sheets

CONTROL VALVE ACTUATED BY LOW-PRESSURE AND LOW-FLOW RATE CONTROL FLUID

FIELD OF THE INVENTION

The present invention relates to a non-electrical control valve which is actuated by low-pressure, and low-flow rate fluids. More particularly, the invention relates to an pneumatically-actuated on/off valve used to control a dental anesthesia/analgesia scavenging system.

BACKGROUND OF THE INVENTION

Pneumatically-actuated on/off or control valves which open and close non-electrically are known in the art. Such valves may include, for example, a piloted actuator which is opened and closed by a pneumatic control fluid source which is connected to an input port on the valve. Movement of the piloted actuator is caused by a pressure differential created across the actuator by the control fluid.

Movement of the actuator may be used to perform a wide variety of functions. For example, movement of the actuator may control the flow of a second fluid source which is connected to a second input port on the valve. This type of valve acts as a "sentry" by "sensing" the input of the control fluid, and then acts as a "trigger" to actuate and/or control the flow of the second fluid through the valve.

Known pneumatically-actuated valves typically include multiple seals, springs, bellows, diaphragms and other internal components which create internal resistance to movement of the actuator. In order to operate properly, such known pneumatically-actuated valves require the input of a high-pressure control fluid which creates a force sufficient to overcome such internal resistance. Further, such internal resistance in prior art valves may spark an explosion if used in an environment containing nitrous oxide, oxygen or other flammable gases. It would be desirable to provide a pneumatically-actuated valve whose design has reduced internal resistance to movement of the actuator.

Many applications require a pneumatically-actuated valve which is responsive to the input of a low-pressure control fluid or a low-flow-rate control fluid. As used herein, "low pressure" is used to refer to pressure slightly above atmospheric pressure and "low flow rate" is used to refer to flow rates of about ½ liter/minute or less. For example, gaseous anesthesia/analgesia provided to a dental patient is typically supplied at a pressure of less than 1 p.s.i. and a flow rate of about 3–10 liters per minute. Prior art pneumatically-actuated valves are typically designated to operate effectively only when connected to a high-pressure control fluid such as 100 p.s.i. It would be desirable to provide a pneumatically-actuated valve which is actuated by the input of a low-pressure or low-flow-rate control fluid such as gaseous anesthesia/analgesia.

As described above, prior art pneumatically-actuated valves have been used to trigger and/or control the flow of a second fluid through the valve. In the dental field, the second fluid typically comprises a mixture of gases exhaled by a patient into an anesthesia/analgesia scavenging mask. The mixture of gases is suctioned from the mask by a vacuum source which is connected to and controlled by an on/off valve. The on/off valve is very hard to initially break free from the closed position because the vacuum source exerts a high suction force on the actuator when the actuator is at or near the closed limit position. To overcome the high suction force, prior art pneumatically-actuated valves require the input of a high pressure control fluid to operate effectively when connected to a high-pressure vacuum fluid source. Therefore, it would also be desirable to provide a pneumatically-actuated valve which can be actuated by a low-pressure control fluid source and when connected to a second high vacuum pressure fluid source.

In many applications, especially dental anesthesia/analgesia applications, the flow rate of control fluid and the flow rate of the second fluid should be proportionally controlled. For example, the flow rate of anesthesia/analgesia delivered to the patient should be proportional to the flow rate of exhalation gases removed by the vacuum source. Prior art pneumatically-actuated valves typically do not automatically regulate the flow rate of the second fluid in proportion to the flow rate of the control fluid. It would also be desirable to provide a pneumatically-actuated valve which is self-regulating so that the flow rate of the second fluid is automatically controlled in proportion to the flow rate of the control fluid.

In dental anesthesia/analgesia applications, it is critical that the vacuum source be activated at or around the same time a supply of anesthesia/analgesia is delivered to the patient. If excess anesthesia/analgesia and exhalation gases from the patient are not scavenged by the vacuum source, a potentially hazardous condition builds up in the treatment room. In prior art anesthesia/analgesia configurations, the vacuum source is activated by a manual control valve which must be opened by an operator independently from the valve controlling the flow of anesthesia/analgesia/analgesia. Not surprisingly, cases have been reported wherein the vacuum-source control valve was not opened during the operation due to human error. Therefore, it would also be particularly desirable to provide a control valve for an anesthesia/analgesia delivery system which automatically activates the anesthesia/analgesia scavenger or vacuum source at the same time anesthesia/analgesia is delivered to a patient.

SUMMARY OF THE INVENTION

The present invention provides a pneumatically-actuated valve which is actuated by the input of a low-pressure or low-flow-rate control fluid such as gaseous anesthesia/analgesia. The valve can be actuated by a low-pressure or low-flow-rate control fluid because its design has reduced internal resistance to movement of a piston actuator. The valve can also be actuated by a low-pressure control fluid source even when connected to a second high-pressure vacuum fluid source. In one embodiment, the valve is also self-regulating so that the flow rate of the second fluid is automatically controlled in proportion to the flow rate of the control fluid. The valve has particular use as a control valve for an anesthesia/analgesia delivery system and automatically activates the anesthesia/analgesia scavenger or vacuum source at the same time anesthesia/analgesia is delivered to a patient.

The valve of the present invention comprises a valve housing having a control-fluid channel and a second-fluid channel. Each channel has an inlet port and an outlet port. The housing has an elongate, cylindrical chamber connecting the control-fluid channel and the second-fluid channel.

The valve has a piston which acts as an actuator to control the flow of fluid through the valve. The piston has a piston head and a piston stem. The piston stem is fixed at one end and extends from the piston head. The other end of the stem is the free end. The piston is movable between open positions and a closed limit position.

The piston stem slides linearly within the cylindrical chamber. The piston stem has a chamber seal which isolates the control-fluid channel from the second-fluid channel when the piston is moved within the cylindrical chamber.

A piston head seat is located intermediate the control-fluid channel. The seat has a shape which compliments the piston head so that the control fluid can flow freely through the control-fluid channel when the piston is in an open position.

The piston head seat has an irregularly-shaped internal surface configuration with multiple internal diameters. Preferably, the piston seat has a double-diameter, stepped configuration. The smallest diameter is slightly larger than the diameter of the piston head and the other diameter is larger than the smallest diameter. The smallest diameter is located at the bottom of the seat. The piston head fits within the smallest diameter at the bottom of the seat but does not contact the bottom of the seat, thereby creating a control-fluid channel plenum underneath the piston head.

A piston stem seat is located intermediate the second-fluid channel. The seat has a shape which compliments the free end of the piston stem so that a fluid seal is formed in the second-fluid channel when the piston is in the closed limit position and so that a second fluid may flow through the second-fluid channel when the piston is in an open position. The piston stem contacts the piston stem seat when the piston is in the closed limit position, thereby creating a positive seal between the control fluid and the vacuum.

The valve is constructed and arranged so that a low-pressure/low-flow-rate control fluid connected to the input port of the control-fluid channel will actuate the piston from the closed limit position to an open position. The valve is also constructed and arranged so that the exhaust-fluid flow channel is automatically opened when the piston is moved to an open position and automatically closed when the piston is moved to the closed limit position.

An annular orifice is formed by the clearance between the outer annular surface of the piston head and the internal surface of the piston head seat. The annular orifice preferably has an equivalent orifice diameter (E) in an open position equal to or smaller than the size of the input port of the control-fluid channel.

The piston head and the piston head seat are constructed and arranged such that the low-pressure control fluid flowing through the orifice creates sufficient back pressure to actuate the piston from the closed limit position to an open position and then maintain the piston in an open position. The back pressure is preferably equal to the minimum back pressure needed to maintain the piston in an open position.

In another embodiment, the piston seat has an upwardly, enlarging tapered configuration. In this embodiment, the valve is constructed and arranged to form a variable annular orifice between the outer annular surface of the piston head and the inner surface of the piston head seat when the piston is actuated to an open position.

The valve automatically adjusts the annular orifice size so that the Bernoules Law force created on the piston is equal to the force necessary to maintain the piston in an open position. The valve is also constructed and arranged so that the opening created in the second-fluid channel is proportional to the opening created in the control-fluid channel when the piston is moved to an open position.

The invention also provides an automated anesthesia/analgesia scavenging system comprising an anesthesia/analgesia source, a vacuum source, a patient scavenging mask in fluid connection with the anesthesia/analgesia source and the vacuum source, and a control valve located intermediate the fluid connection between the mask and the anesthesia/analgesia source and the vacuum source. The control valve has the same construction as described above.

The anesthesia/analgesia scavenging system is constructed and arranged so that a low-pressure/low-flow-rate anesthesia/analgesia source connected to the input port of the anesthesia/analgesia channel of the valve will actuate the piston from the closed limit position to an open position. The valve is also constructed and arranged so that the vacuum channel is automatically opened when the piston is moved to an open position, and so that the vacuum channel is automatically closed when the piston is moved to the closed limit position.

DETAILED DESCRIPTION OF PREFERRED EMBODIMENTS

For the purpose of illustration, preferred embodiments of the claimed invention are shown in FIGS. 1–8 wherein like numerals are used to designate like parts throughout the drawings.

Figure 1:
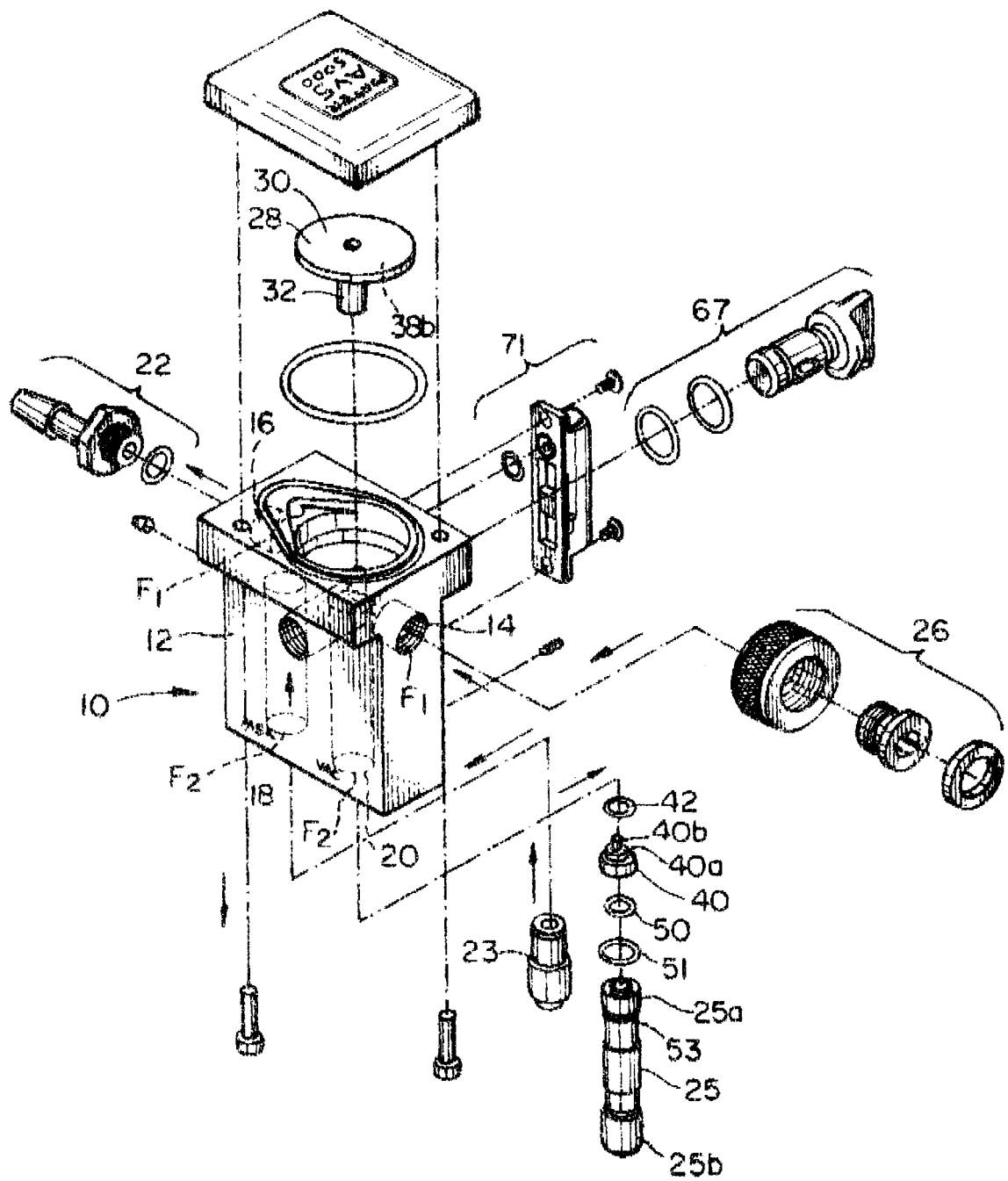
FIG. 1 is an exploded, assembly diagram of a pneumatically-actuated valve in accordance with an embodiment of the present invention.

A first embodiment of the invention is illustrated in FIG. 1 wherein the pneumatically-actuated control valve of the present invention is designated generally by reference numeral 10. The valve 10 shown in FIG. 1 is an on/off type valve designed to be actuated by the input of a low-pressure/low-flow-rate control fluid (such as anesthesia/analgesia) and then trigger the flow of a second fluid. The second fluid may be, for example, patient exhalation gases withdrawn by a vacuum source from a patient scavenging mask.

Figure 4:
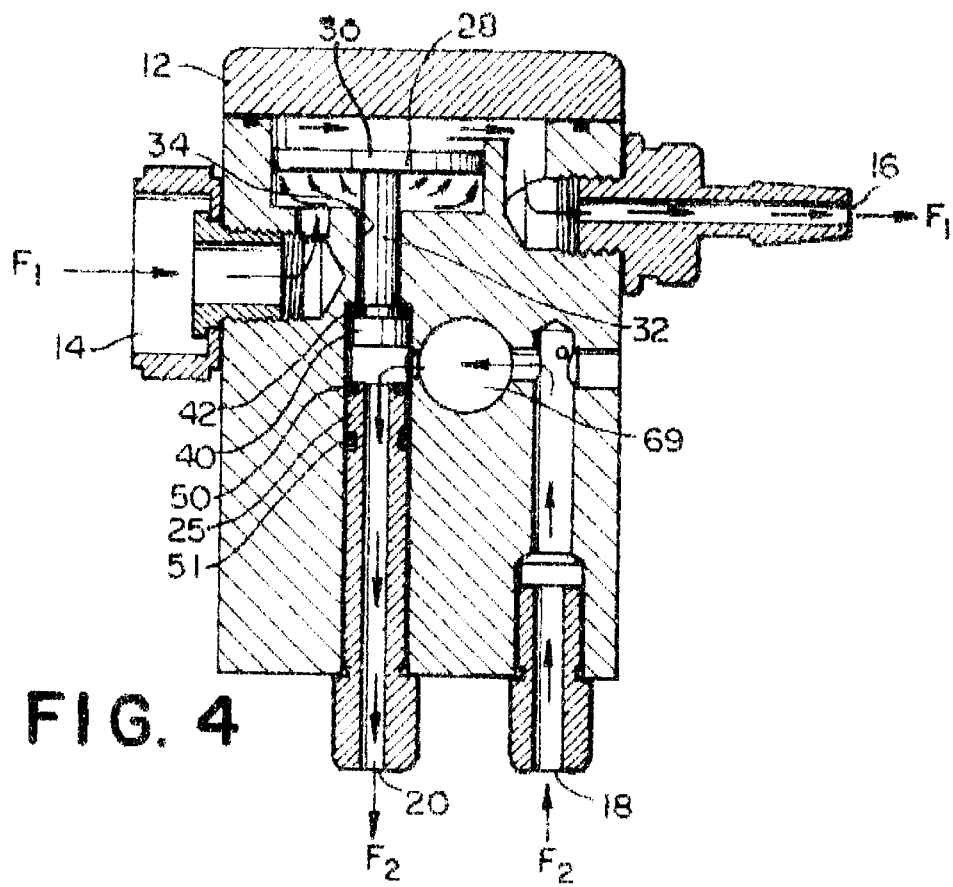
FIG. 4 is a schematic illustration of the valve in an open position in accordance with an embodiment of the invention.

The control valve 10 has an irregularly-shaped valve body or housing 12. The housing 12 has multiple internal chambers formed therein which are connected to form a first flow channel for a control fluid and a second flow channel for a second fluid. Referring to FIG. 4, the first flow channel is designated by reference numeral F1 and is illustrated with fluid flow lines. The second flow channel is designated by reference numeral F2 and is also illustrated by fluid flow lines.

The first flow channel F1 has an inlet port 14 and an outlet port 16. Similarly, the second flow channel F2 has an inlet port 18 and an outlet port 20.

Figure 5:
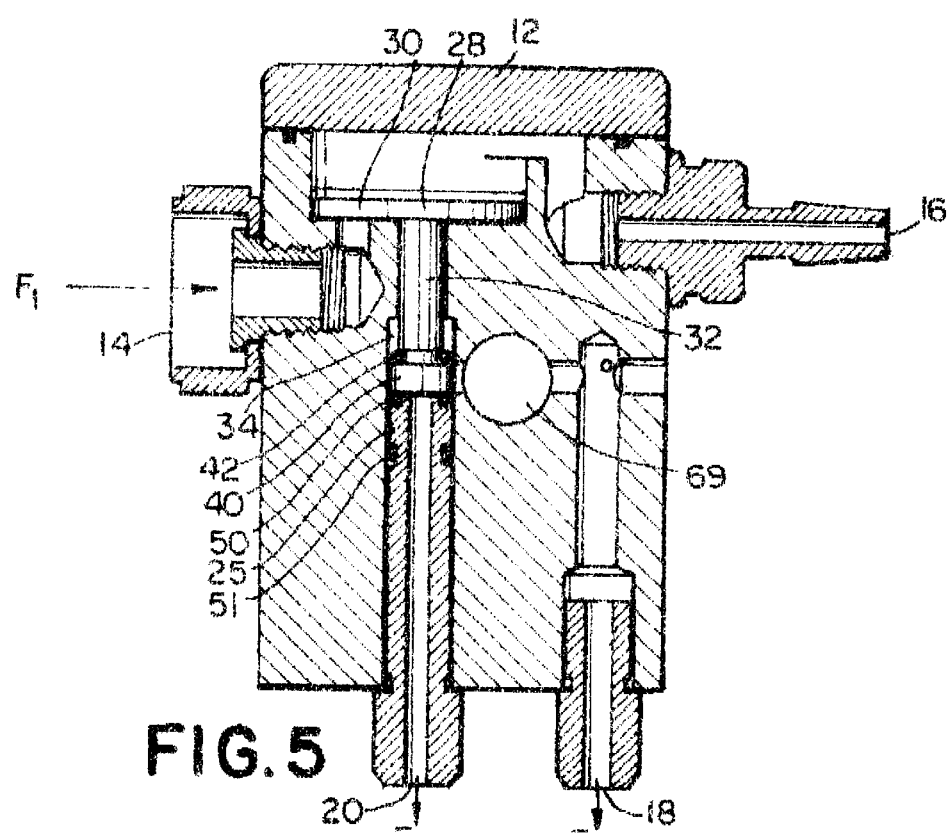
FIG. 5 is a schematic illustration of the valve in the closed limit position in accordance with an embodiment of the invention.
Figure 6:
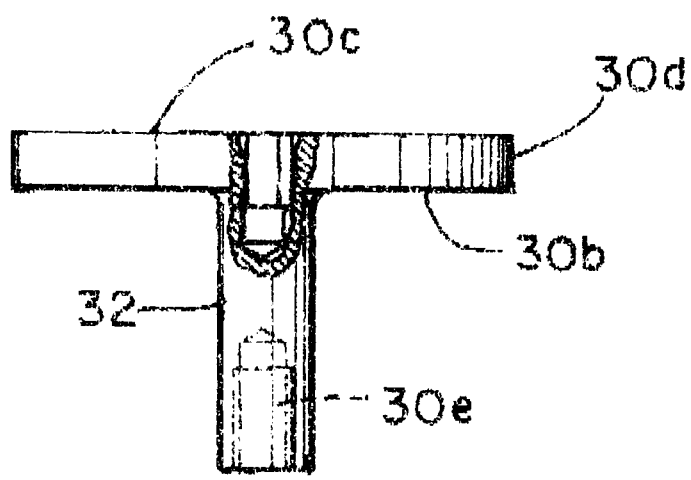
FIG. 6 is an enlarged, side elevation and fragmentary cross-sectional view of the piston shown in FIG. 1.
Figure 7:
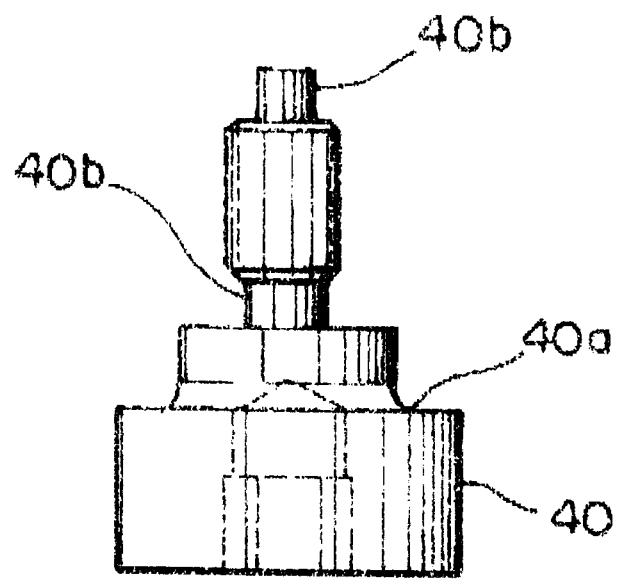
FIG. 7 is an enlarged, side-elevational view of the piston chamber seal shown in FIG. 1.

The inlet port 14 and outlet port 16 of the first flow channel preferably comprise threaded bores extending into the housing 12 and are designed to receive threaded adapters such as a canula connector assembly 22, and a threaded seal nut assembly 26. The inlet port 18 and outlet port 20 of the second flow channel F2 are preferably non-threaded bores extending into the housing 12 and are designed to receive cylindrical stem connectors 23, 25. As described below in greater detail, fluid flow through the first and second channels is controlled by a piston 28 which is linearly movable within an elongate cylindrical bore or chamber 34 in the housing 12. The piston 28 is movable between open positions, one of which is shown in FIG. 4, and a closed limit position which is shown in FIG. 5.

The piston 28 has a circular, disk-like head 30 and an elongate, cylindrical stem 32. The piston stem 32 comprises an elongate, cylindrical, rod fixed at one end and extending from the center of the bottom side 38b of the piston head 30. The other end of stem is the free end and is connected to a chamber seal (described below).

Figure 2:
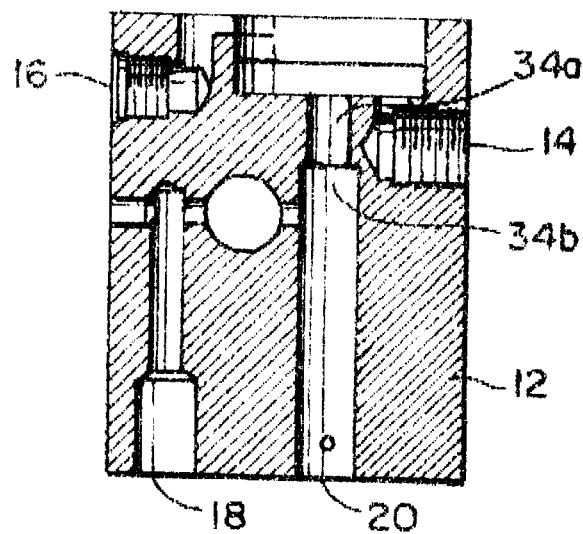
FIG. 2 is a cross-sectional view of the housing of a valve in accordance with an embodiment of the invention.

The piston stem 32 is guided by and travels within an elongate, stepped, cylindrical bore or piston chamber 34 which is located intermediate the first and second fluid flow channels. Referring to FIG. 2, the diameter of the upper portion 34a of the piston chamber 34 is slightly larger then the diameter of the stem 32. The lower portion 34b of the piston chamber 34 has an enlarged diameter. The piston chamber 34 would connect the first fluid flow channel F1 and the second fluid flow channel F2 if a chamber seal was not located therein.

The chamber seal is fixed to the free end of the piston stem 32. The chamber seal isolates the first fluid flow channel F1 from the second fluid flow channel F2. In a preferred embodiment, the chamber seal comprises an O-ring 42 and an O-ring retainer 40. The O-ring retainer 40 has a protruding teat 40b which is inserted into a bore in the free/lower end of the piston stem 32. The retainer 40 has a stepped seat 40a on which the O-ring is secured. The chamber seal travels upwardly and downwardly within the lower portion 34b of the piston chamber 34 while still maintaining the two channels F1 and F2 in fluid isolation.

The bottom portion of the O-ring retainer 40 is constructed to seal against a piston stem seat located intermediate the second fluid flow channel F2. In a preferred embodiment, the piston stem seat comprises the upper end 25a of the exit port stem connector 25. The exit port stem connector 25 comprises a hollow, cylindrical tube having a stepped seat 25a on one end and a stepped flange 25b on the other end. An O-ring seal 50 is secured on the stepped seat 25a. A second O-ring seal 51 is seated in an annular recess 53 on the outer circumference of the stem connector 25. The stepped flange 25b helps locate the exit port stem connector 25 in the exit port 20 at the desired location so that the O-ring retainer stem 40 contacts the O-ring 50 of the piston stem seat when the piston is in the closed limit position.

Referring to FIG. 5, the O-ring retainer stem 40 contacts the O-ring seal 50 when the piston is in the closed limit position, thereby blocking the flow of any fluid through the second fluid flow channel F2. Referring to FIG. 4, when the piston is moved upwardly to one of the open positions, the stem retainer 40 moves out of contact with the O-ring seal 50, thereby opening the second fluid flow channel F2.

The piston head 30 travels upwardly and downwardly within an enlarged-diameter, upper portion of the housing generally referred to as the piston seat 44. In operation, the piston head 30 preferably does not contact the bottom of the seat. Rather, a control-fluid channel plenum 45 is created between the bottom of the seat 44 and the bottom of the piston head 30. The piston head seat 44 is formed in the first fluid flow channel F1 intermediate the inlet port 14 and outlet port 16. The piston head seat 44 is designed so that the control fluid may flow freely through the first fluid flow channel F1 when the piston is moved upwardly to an open position as seen, for example, in FIG. 4.

Figure 3:
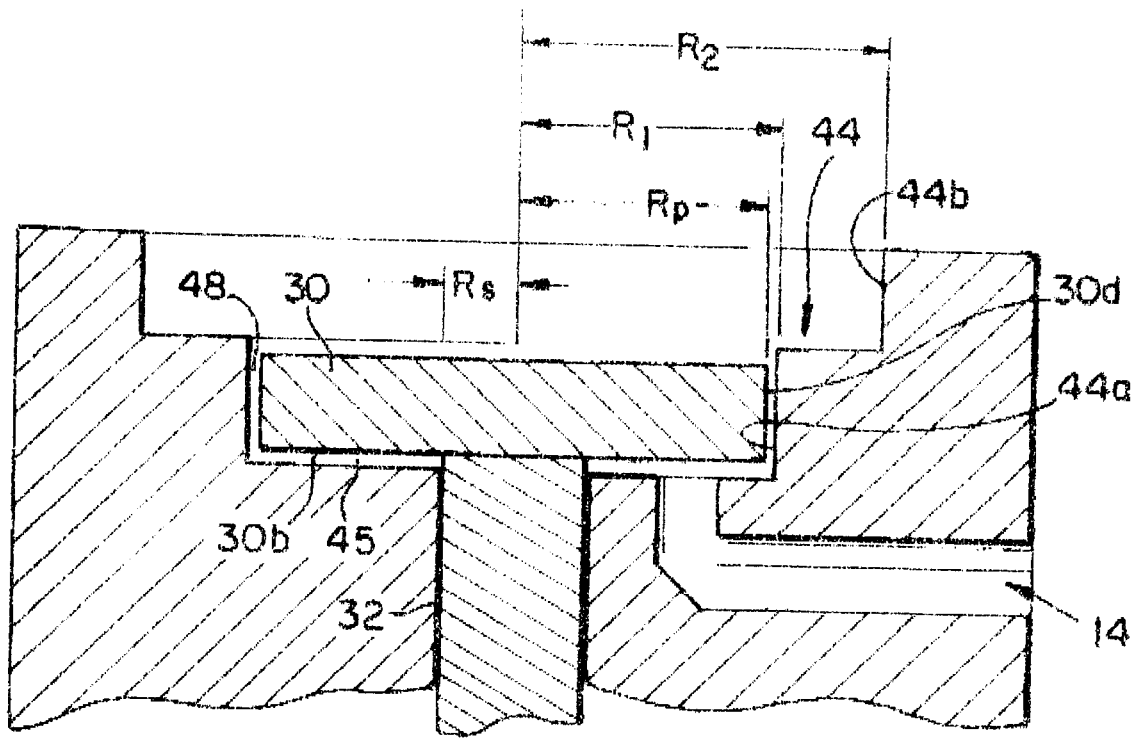
FIG. 3 is an enlarged, schematic, cross-sectional view of a piston and piston head seat of a valve in accordance with an embodiment of the invention.

Referring to FIG. 3, the piston head seat 44 preferably has a double-diameter, stepped configuration. The first or lower radius $R_1$ of the seat 44, is slightly larger than the radius $R_p$ of the piston head 30. The second or upper radius $R_2$ is slightly larger than the lower radius $R_1$.

Referring to FIG. 3, when the piston is in the closed limit position, an enlarged lower chamber or plenum 45 is formed between the bottom surface 30b of the piston head 30 and the bottom of the piston head seat 44. The enlarged chamber 45 is connected to the input port 14. The enlarged lower chamber or plenum 45 is provided so that a low pressure or low flow rate control fluid introduced therein will produce an upward or opening force on the piston head defined by the equation: force upward (F)=pressure of the control fluid (P) x area of piston (A). Referring to FIG. 3, the lower area of the piston A is equal to $\pi(R_p^2-R_s^2)$ where $R_p$ is the radius of the piston head and $R_s$ is the radius of the piston head stem. The dimensions of the valve seat and piston may be selected so that the upward force created by the control fluid is sufficient to move the piston upwardly against the weight of the piston and against the suction force on the piston from the second fluid flow channel F2 (described below).

The piston head seat 44 is also designed so that an annular orifice 48 is created around the piston head so that the incoming control fluid can pass evenly under the piston head and flow laminarly through the annular orifice 48. The annular orifice is created by the clearance between the outer annular surface 30d of the piston head 30 and the inner surfaces 44a, 44b of the piston head seat 44.

The flow of control fluid through the annular orifice 48 creates a pressure drop across the piston head governed by Bernoules Law. The flow of control fluid through the annular orifice 48 creates an upward force sufficient to actuate the piston upwardly to an open position and keep the valve open. When the piston head is at a vertical position proximate the lower portion of the seat (closed position), the orifice size is smaller than when the piston head is in a vertical position proximate the upper portion of the seat (open position) since $R_2$ is greater than $R_1$. Therefore, the upward force on the piston is greater in the closed position than in the open position.

The piston head and the piston head seat are designed so that the upward force on the piston in the closed position is sufficient to raise the piston to the open position, and the upward force on the piston in the open position is equal to or slightly greater than the force necessary to hold the valve up in the open position. Thus, the dimensions of the piston head seat 44 and piston head 30 should be selected so that the equivalent orifice diameter(E) in the open position is slightly smaller than the size of the input port. The equivalent orifice diameter created by the clearance between the piston head 30 and the upper portion of the piston head seat 44 is governed by the equation: equivalent orifice diameter $(E)=(D_2^2-D_p^2)^{1/2}$.

In the fully-open position, the piston stem O-ring 42 contacts the internal shoulder between the upper 34a and lower portions 34b of the piston chamber 34, thereby preventing the piston 28 from moving upwardly beyond a desired vertical position. More importantly, in the fully-open position, the back pressure created by the piston does not significantly restrict the flow of low-pressure control through the first flow channel F1.

Referring to FIGS. 4 and 5, it can be seen that the single piston automatically opens the second fluid flow channel F2 when a flow of control fluid is introduced into the first fluid flow channel F1. To insure this function, the piston stem 32 should preferably be dimensioned such that the entirety of the free end of the piston stem 32 moves upwardly out of the second flow channel F2 when the piston is in the open position as seen in FIG. 4. Otherwise, the second fluid flow channel F2 will remain partially obstructed.

The valve of the present invention may also be provided with a vacuum control adjustment toggle control valve assembly 67 which is located in a bore 69 intermediate the second fluid flow channel F2. The valve assembly 67 may include a flow meter assembly 71.

Figure 9:
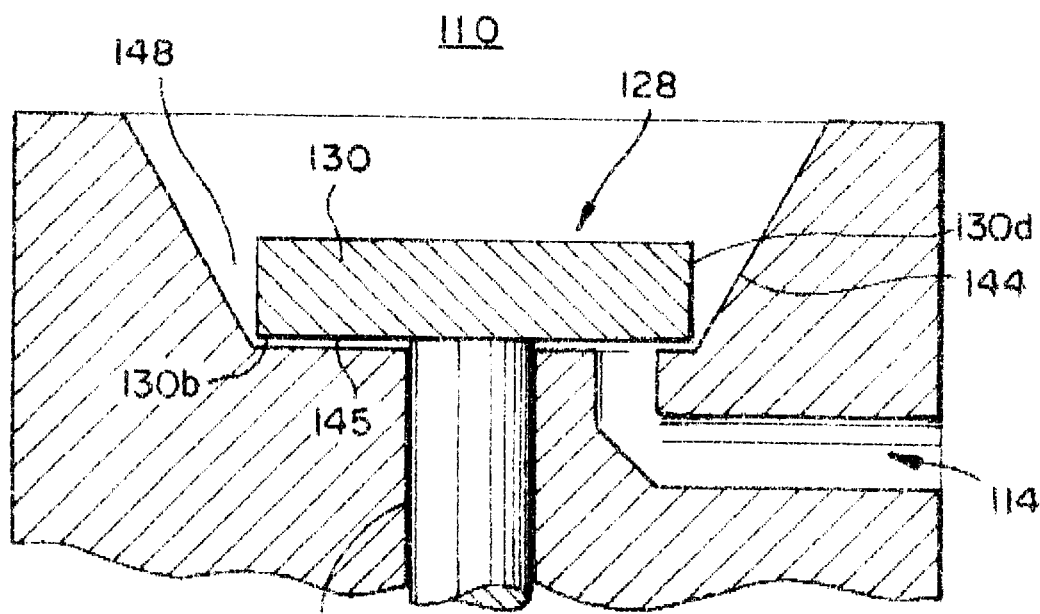

In a further embodiment of the invention, shown in FIG. 9, the valve is also self-regulating, i.e., the control of fluid through the second channel F2 is controlled in proportion to the flow of control fluid through the first channel F1.

In this embodiment, the degree of occlusion of the second fluid flow channel depends on the distance travelled upwardly by the piston 128. As the pressure or flow rate of the control fluid increases, the piston 128 will travel upwardly further. As a direct result, the piston stem 132 also travels upwardly further and is withdrawn further from the second channel F2, thereby creating a greater opening in the second channel F2.

Upward movement of the piston 128 is controlled by the tapered shape of the seat 144. As the piston travels upwardly further, the annular orifice 148 becomes larger, thereby reducing the Bernoules law force on the piston 128. The dimensions of the piston head seat 144 are therefore selected to control the stroke of the piston 128.

Referring to FIG. 9, this embodiment is similar in construction to the embodiment illustrated above in FIGS. 1–6 except that the piston head seat 144 has an upwardly enlarging tapered configuration. Otherwise, the operation and construction of the valve 110 is similar to the previously discussed valve 10.

In a further embodiment of the invention, the second flow channel F2 may have the inlet port and the outlet port reversed from the first embodiment 10 described and illustrated above. In this embodiment, the piston's upward movement is not restricted as much by the downward force created by the vacuum source. In this embodiment, the piston 28 could be actuated from its closed position to its open position with an even lower pressure and flow rate of the control fluid than in the previous embodiments.

Figure 8:
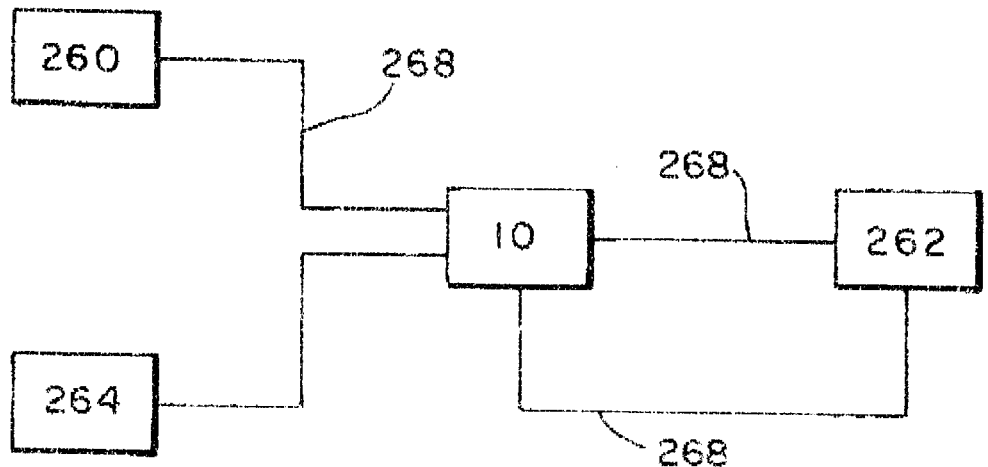
FIG. 8 is a schematic illustration of an anesthesia/analgesia system in accordance with another embodiment of the invention; and, FIG. 9 is an enlarged, schematic, cross-sectional view of a piston and piston head seat of a valve in accordance with a further embodiment of the invention.

The present invention also provides an anesthesia/analgesia scavenging system which has particular application to the dental anesthesia/analgesia fields. Referring to FIG. 8, the system has an anesthesia/analgesia source 260 connected to the input port of the first fluid flow channel F1 of the control valve 10. The exit port of the first fluid flow channel F1 of the control valve is connected by a flexible, hollow tubing 268 to a patient scavenging mask 262 which is placed over a patient's mouth and/or nose. Through this connection, a supply of anesthesia/analgesia is provided to the patient.

A vacuum source 264 is connected to the output port of the second fluid flow channel F1 of the valve 10. The input port of the second fluid flow channel F2 is also connected to the patient scavenging mask 262. Through this connection, unused anesthesia/analgesia and gases exhaled by the patient are collected and removed from the treatment room.

During a dental procedure, the dentist initially provides the patient with anesthesia/analgesia by opening the anesthesia/analgesia source 260. This low pressure control fluid causes the piston to move upwardly, thereby opening the first fluid flow channel. Simultaneously, the second fluid flow channel is opened as the piston head moves upwardly. Once the supply of anesthesia/analgesia is turned off by the dentist, the piston drops back down to the closed limit position, thereby closing the second fluid flow channel F2.

What is claimed is:

1. An automated anesthesia/analgesia scavenging system comprising:

a) an anesthesia/analgesia source;

b) a vacuum source;

c) a patient scavenging mask in fluid connection with said anesthesia/analgesia source and said vacuum source;

d) a control valve located intermediate the fluid connection between said mask and said anesthesia/analgesia source and said vacuum source; said control valve comprising:

a) a valve housing having an anesthesia/analgesia channel and a vacuum channel, each channel having an inlet port and an outlet port, b) a piston comprising a piston head and a piston stem having one end fixed to and extending from said piston head and a free end, said piston being movable between open positions and a closed limit position;

c) a piston head seat located intermediate said anesthesia/analgesia channel, said seat having a shape which compliments said piston head so that the control fluid can flow through said anesthesia/analgesia channel when said piston is in an open position;

d) a piston stem seat located intermediate said vacuum channel, said seat having a shape which compliments said free end of said piston stem so that a fluid seal is formed in said vacuum channel when said piston is in the closed limit position and so that exhaled respiratory gases may flow through said vacuum channel when said piston is in an open position;

said valve constructed and arranged so that a low-pressure/low-flow-rate anesthesia/analgesia connected to the input port of said anesthesia/analgesia channel will actuate said piston from the closed limit position to an open position, said valve constructed and arranged so that said vacuum channel is automatically opened when said piston is moved to an open position, and said second-fluid channel is automatically closed when said piston is moved to said closed limit position.

* * * * *